United States Patent [19]

Tucker et al.

[11] Patent Number: 4,590,007

[45] Date of Patent: May 20, 1986

[54] FLURONAPHTHALENE CHROMIUM TRICARBONYLS USEFUL AS HYDROGENATION CATALYSTS FOR POLYUNSATURATED FATTY ACID RESIDUE-CONTAINING COMPOSITIONS

[75] Inventors: James R. Tucker; Dennis P. Riley, both of Cincinnati, Ohio

[73] Assignee: The Procter & Gamble Company, Cincinnati, Ohio

[21] Appl. No.: 632,775

[22] Filed: Jul. 20, 1984

[51] Int. Cl.$^4$ .............................................. C11C 3/12
[52] U.S. Cl. ...................................... 260/409; 556/60
[58] Field of Search ........................ 260/409, 429 AR; 556/60

[56] References Cited

U.S. PATENT DOCUMENTS

| 3,381,023 | 4/1968 | Whiting | 260/429 R |
| 3,382,263 | 5/1968 | Pruett et al. | 260/429 R |
| 3,539,647 | 11/1970 | Whiting et al. | 260/429 R |
| 3,542,821 | 11/1970 | Frankel . | |
| 3,632,614 | 1/1972 | Cais et al. . | |
| 3,911,023 | 10/1975 | Farona et al. . | |

OTHER PUBLICATIONS

Cais et al., "The Catalytic Activity of Tricarbonyl Chromium Complexes of Phenanthrene, Naphthalene and Anthracene in the Hydrogenation of Dienes," *Coor. Chem. Rev.*, vol. 16, (1975), pp. 27-34.
Yagupsky et al., "Solvent-Assisted Regioselective and Stereospecific Hydrogenation of Dienes, at Ambient Temperatures and Pressures Catalyzed by Naphthalene Cr(CO)$_3$, Nature of the Active Catalytic Species," *Inorg. Chim. Acta*, vol. 12, (1975) pp. 127-128.
Eden et al., "Stereospecific and Regioselective Hydrogenation of Bicyclo(2.2.1) Hepta-2,5-Diene and Related Systems Catalyzed by Tricarbonyl Chromium Complexes of Phenanthrene and Naphthalene," *Israel J. Chem.*, vol. 25, (1977), pp. 223-229.
Ranguis et al., "Study on the Hydrogenation and Hydroformulation of Deinic Synthesi Esters Catalyzed by Carbonyl Complexes," *Actes Congr. Mond.—Soc. Int. Etude Corp. Gras.*, 13th, Sect. E, (1976), pp. E35-E42.
Frankel et al., "Homogeneous Catalytic Hydrogenation of Unsaturated Fats: Group VIB Metal Carbonyl Complexes," *J. Am. Oil Chem. Soc.*, vol. 46, (1969), pp. 256-261.
Cais et al., "Organometallic Studies: Selective Hydrogenation of Conjugated Olefins Catalyzed by Arene Chromium Tricarbonyl Complexes," *Tet. Lett.*, (1968), pp. 1919-1923.
Cais et al., "Organometallic Studies: Selective Hydrogeantion of Dienes Catalyzed by Arene Chromium Tricarbonyl Complexes," *Inorg. Chim Acta*, vol. 4, (1970), pp. 509-516.
Deubzer et al., "Spektroskopische Untersuchungeran Mettalorganischen Verbindunger: H-NMR-Spektron von Naphthalin-Chromo(O)-Tricarbonyl und Seinen Derivaten," *J. Organometal. Chem.*, vol. 7, (1967), pp. 289-299.
Frankel et al., "Homogeneous Hydrogenation of Diolefins Catalyzed by Tricarbonyl Chromium Complexes: Stereoselective 1,4 Addition of Hydrogen," *J. Org. Chem.*, vol. 34, (1969), pp. 3930-3936.
Frankel et al., "Selective Homogeneous Hydrogenation of Triunsaturated Fats Catalyzed by Tricarbonyl Chromium Complexes," *J. Am. Oil Chem. Soc.*, vol. 49, (1972), pp. 70-74.
Frankel, "Homogeneous Catalytic Conjugation of Polyunsaturated Fats by Chromium Carbonyls," *J. Am. Oil Chem. Soc.*, vol. 47, (1970), pp. 33-36.
Frankel et al., "Homogeneous Hydrogenation of Diolefins Catalyzed by Tricarbonyl Chromium Complexes: Deuteration," *J. Org. Chem.*, vol. 34, (1969), pp. 3936-3942.
Frankel, "Conversion of Polyunsaturates and Vegetable Oils to cis-Monounsaturates by Homogeneous Hydrogenation Catalyzed with Chromium Carbonyls," *J. Am. Oil Chem. Soc.*, vol. 47, (1970), pp. 11-14.
Frankel et al., "Stereoselective Hydrogenation of Model Compounds and Preparation of Tailor-Made Glycerides with Chromium Tricarbonyl Complexes," *J. Am. Oil Chem. Soc.*, vol. 47, (1970), pp. 497-500.
Mahaffy et al., "Phenylation Using Fluorobenzene Tricarbonyl Chromium," *J. Chem. Res. Synop.*, 1979, Issue 4, p. 128 (*Chem. Abs.* 92:6647n).
Card et al., "Arene-Metal Complexes: Reaction of Substituted (Benzene)-Tri-Carbonyl Chromium Complexes with n-Butyllithium," *J. Org. Chem.*, vol. 45, (1980), pp. 2560-2566.
*Chem. Abs.*, 58:5709 (1963).
Chem. Abs., 71:117669g (1969).
Mahaffy et al., "(n$^6$-Arene)Tricarbonyl Chromium Complexes," *Inorg. Syn.*, vol. 19, (1979), pp. 154-158.
Khandkarova et al., "Effective Coordination with the Metal on the Reactivity of $\pi$-Bonded Organic Ligands: Determination of the Inductive Constant for the (CO)$_3$CrC$_6$H$_5$-Substituent by $^{19}$F NMR Method," *J. Organomet. Chem.*, vol. 23, (1970), pp. 509-515.

(List continued on next page.)

*Primary Examiner*—Helen M. S. Sneed
*Attorney, Agent, or Firm*—Eric W. Guttag; Steven J. Goldstein; Richard C. Witte

[57] ABSTRACT

Fluronaphthalene chromium tricarbonyls useful as hydrogenation catalysts are disclosed. Compositions suitable for hydrogenation comprise glycerides, nonglyceride esters, or mixtures thereof having polyunsaturated fatty acid residues, in particular polyunsaturated vegetable oils and those containing methyl linoleate. After being placed in a reactor having an inert inner surface, the polyunsaturated fatty acid residue-containing composition is contacted with hydrogen in the presence of the fluoronaphthalene chromium tricarbonyl to effect hydrogenation of the polyunsaturated fatty acid residues.

17 Claims, No Drawings

OTHER PUBLICATIONS

Lumbroso et al., "An Experimental Study of Various Arene Tricarbonyl Chromium Complexes," *J. Organomet. Chem.*, vol. 165, (1965), pp. 341–351.

Adcock et al., "$^{13}$C and $^{19}$F NMR Substituent Chemical Shifts (SCS) of Some Bridge Head-Substituted Phenyl- and Fluorophenylbicyclo-(2.2.2)Octyltricarbonyl Chromium (O) Derivatives: Nature of Aryl $^{19}$F NMR Polar Field Effects in the CR(CO)$_3$-Complexed Benzene Ring System," *J. Organomet. Chem.*, vol. 201, (1980), pp. 411–431.

Jaouen et al., "Means of Determination of Configuration for Optically Active Benchrotrene Compounds," *J. Organometal. Chem.*, vol. 21, (1970), pp. P43–P46.

FLURONAPHTHALENE CHROMIUM TRICARBONYLS USEFUL AS HYDROGENATION CATALYSTS FOR POLYUNSATURATED FATTY ACID RESIDUE-CONTAINING COMPOSITIONS

TECHNICAL FIELD

The present application relates to the hydrogenation of polyunsaturated fatty acid residue-containing compositions, such as polyunsaturated vegetable oils and those containing methyl linoleate, using fluoronaphthalene chromium tricarbonyl catalysts.

Polyunsaturated fatty acid containing compounds are frequently hydrogenated to their more oxidatively stable monounsaturated products. Particularly important examples are the glyceride and non-glyceride esters of linoleic acid (cis,cis-9,12-octadecadienoic acid) and to a lesser extent linolenic acid (cis,cis,cis-9,12,15-octadecatrienoic acid). The hydrogenation of linoleic and linolenic acid-containing glycerides prevents oxidative flavor deterioration of a vareity of polyunsaturated vegetable oils such as soybean oil, safflower oil and sunflower seed oil. Also, the hydrogenation of methyl linoleate (present in the mixed methyl esters of tall oil fatty acids) to methyl isooleates can be used to produce isooleic acid mixtures similar in properties to oleic acid.

In the case of polyunsaturated vegetable oils, nickel catalysts are typically used for partial hydrogenation. See Bailey's Industrial Oil and Fat Products, (3rd edition 1964), pp. 793 et seq. However, these nickel catalysts do not selectively hydrogenate the polyunsaturated fatty acid residues to the desired cis-monounsaturated fatty acid residues. Instead, a significant amount of higher melting trans-unsaturated glycerides are formed due to isomerization of the polyunsaturated fatty acid residues. Because these partially hydrogenated vegetable oils are often used in cooking and salad oil preparation, a separate winterization step can be required to remove these higher melting trans-unsaturated glycerides.

Instead of nickel catalysts, benzene and methyl benzoate chromium tricarbonyl complexes have been used as catalysts to more selectively hydrogenate the polyunsaturated fatty acid residues of vegetable oils to provide less of the undesirable trans-unsaturated glycerides. See U.S. Pat. No. 3,542,821 to Frankel, issued Nov. 24, 1970. These catalysts have also been used for selective hydrogenation of methyl linoleate to the methyl isooleates. See Frankel et al., "Homogeneous Hydrogenation of Diolefins Catalyzed by Tricarbonyl Chromium Complexes: Selective 1,4 Addition of Hydrogenation," *J. Org. Chem.*, Vol. 34, (1969), pp. 3930–36.

Even using these more selective benzene and benzoate chromium tricarbonyl catalysts, a significant amount of trans-unsaturated fatty acid residues are formed, typically from 3–9% for the partially hydrogenated vegetable oils (see U.S. Pat. No. 3,542,821, supra at column 3, lines 3–5) and from 6–12% for the hydrogenation of methyl linoleate (See Frankel et al., supra at p. 3933). It is believed that the temperatures (160°–175° C.) typically employed for hydrogenation with these catalysts promote the isomerization of the polyunsaturated fatty acid residues to the respective trans-unsaturates. At lower temperatures such as 120°–140° C., isomerization of the polyunsaturated fatty acid residues is less favored. However, these benzene and benzoate chromium tricarbonyl complexes are less effective hydrogenation catalysts at these lower temperatures. It would therefore be desirable to find a catalyst which provides more effective hydrogenation of these polyunsaturated fatty acid residues at lower temperatures which do not favor isomerization.

BACKGROUND ART

A. Hydrogenation of Dienes Using Naphthalene Chromium Tricarbonyl as the Catalyst Cais et al., "The Catalytic Activity of Tricarbonyl Chromium Complexes of Phenanthrene, Naphthalene and Anthracene in the Hydrogenation of Dienes," *Coord. Chem. Rev.*, Vol. 16, (1975), pages 27–34, discloses kinetic studies on the hydrogenation of dienes using arene chromium tricarbonyls as catalysts, including naphthalene chromium tricarbonyl. The hydrogenation of methyl sorbate, a conjugated diene, was carried out at temperatures ranging from 27° to 120° C. in solvents such as decalin, tetrahydrofuran (THF) and acetone. In addition, naphthalene chromium tricarbonyl was used to catalyze the hydrogenation of 1,4-cyclohexadiene in acetone at a temperature of 40.5° C.; the reaction rate and induction time data suggest that this reaction was extremely sluggish. See also Yagupsky et al., "Solvent-Assisted Regioselective and Stereospecific Hydrogenation of Dienes, at Ambient Temperatures and Pressures Catalyzed by (Naphthalene) $Cr(CO)_3$; Nature of the Active Catalytic Species," *Inorg. Chim. Acta*, Vol. 12, (1975), pages L27–L28, which also discloses the hydrogenation of methyl sorbate at 30° C. and one atmosphere total pressure using naphthalene chromium tricarbonyl as the catalyst.

Eden et al., "Stereospecific and Regioselective Hydrogenation of Bicyclo[2.2.1]Hepta-2,5-Diene and Related Systems Catalyzed by Tricarbonyl Chromium Complexes of Phenanthrene and Naphthalene," *Israel J. Chem.*, Vol. 25, (1977), pp. 223–29, discloses the hydrogenation of norbornadiene and related bicyclic compounds using naphthalene chromium tricarbonyl as the catalyst. Nortricylene was the major product formed (82%) with the minor product being norbornene (18%). This reaction was carried out at a temperature of 30.2° C. in THF.

B. Hydrogenation of Conjugated Diene Esters Using Fluorobenzene Chromium Tricarbonyl as the Catalyst Ranguis et al., "Study on the Hydrogenation and Hydroformulation of Dienic Synthesis Esters, Catalyzed by Carbonyl Complexes," *Actes Congr. Mond.—Soc. Int. Etude Corps Gras 13th, Sect. E*, (1976), pp. E35–E42, discloses the catalytic hydrogenation of the ethyl ester of 4-methyl-2,4-heptadienoic acid using various chromium tricarbonyl complexes as catalysts. The results from the hydrogenation of this ethyl ester using fluorobenzene and chlorobenzene chromium tricarbonyl at temperatures of from 120° C.–160° C. is shown in the following table:

| Catalyst | Temp. (°C.) | % Conversion | % Monoene Ester |
|---|---|---|---|
| Fluorobenzene | 120 | 41 | 41 |
|  | 140 | 100 | 98 |
|  | 160 | 100 | 97 |
| Chlorobenzene | 120 | 30 | 38 |
|  | 140 | 100 | 97 |
|  | 160 | 100 | 95 |

See also U.S. Pat. No. 3,632,614 to Cais et al., issued Jan. 4, 1972 (hydrogenation of conjugated diene esters, including methyl sorbate, using chlorobenzene chromium tricarbonyl as the catalyst); Frankel, "Homogeneous Catalytic Hydrogenation of Unsaturated Fats: Group VIB Metal Carbonyl Complexes," *J. Am. Oil Chem. Soc.*, Vol. 46, (1969), pp. 256–61 (hydrogenation of methyl sorbate using chlorobenzene chromium tricarbonyl as the catalyst); Cais et al., "Organometallic Studies: Selective Hydrogenation of Conjugated Olefins Catalyzed by Arene Chromium Tricarbonyl Complexes," *Tet. Lett.*, (1968), pp. 1919–23 (similar disclosure); Cais et al., "Organometallic Studies: Selective Hydrogenation of Dienes Catalyzed by Arene Chromium Tricarbonyl Complexes," *Inorg. Chim. Acta*, Vol. 4, (1970), pp. 509–16 (similar disclosure).

C. Fluoronaphthalene Tricarbonyl Chromium Complexes

Deubzer et al., "Spektroskopische Untersuchunger an Metallorganischen Verbindunger: H-NMR-Spektren von Naphthalin-Chromo(O)-Tricarbonyl und Seinen Derivaten," *J. Organometal. Chem.*, Vol. 7, (1967), pp. 289–99, discloses a variety of arene chromium tricarbonyl complexes. Included in this disclosure is 1,4-trifluoronaphthalene chromium tricarbonyl.

D. Hydrogenation of Methyl Linoleate Using Benzene and Methyl Benzoate Chromium Tricarbonyl Complexes as Catalysts Frankel et al., "Homogeneous Hydrogenation of Diolefins Catalyzed by Tricarbonyl Chromium Complexes: Stereoselective 1,4 Addition of Hydrogenation," *J. Org. Chem.*, Vol. 34, (1969), pp. 3930–36, discloses the hydrogenation of various dienes using benzene and methyl benzoate chromium tricarbonyl complexes as the catalysts. Methyl linoleate was hydrogenated to methyl isooleates using both of these complexes under the following conditions:

| Complex | Temp. (°C.) | Time (hr) | Isooleates (%) | Trans Unsaturates (%) |
|---|---|---|---|---|
| methyl benzoate | 175 | 3 | 94.8 | 12.4 |
| benzene | 165 | 8 | 79.0 | 6.1 |

See also Frankel et al., "Selective Homogeneous Hydrogenation of Triunsaturated Fats Catalyzed by Tricarbonyl Chromium Complexes," *J. Am. Oil Chem. Soc.*, Vol. 49, (1972), pp. 70–74 (hydrogenation of methyl linolenate at temperatures of from 165°–175° C. in cyclohexane using methyl benzoate chromium tricarbonyl as the catalyst; trans-unsaturated content ranged from 17.8–39.5%); Frankel et al., "Homogeneous Catalytic Hydrogenation of Unsaturated Fats: Group VIB Metal Carbonyl Complexes," *J. Am. Oil Chem. Soc.*, Vol. 46, (1969), pp. 256–61 (hydrogenation of methyl esters of soybean oil at temperatures of from 165°–175° C. in hexane using benzene and methyl benzoate chromium tricarbonyl complexes as catalysts; trans-unsaturate content ranged from 3.5–15.4%); Frankel, "Homogeneous Catalytic Conjugation of Polyunsaturated Fats by Chromium Carbonyls," *J. Am. Oil Chem. Soc.*, Vol. 47, (1970), pp. 33–36 (conjugation of methyl linoleate in hexane at temperatures of from 165°–185° C. using benzene and methyl benzoate chromium tricarbonyl complexes as catalysts); Frankel et al., "Homogeneous Hydrogenation of Diolefins Catalyzed by Tricarbonyl Chromium Complexes: Deuteration," *J. Org. Chem.*, (1969), pp. 3936–42 (deuteration of methyl linoleate at temperatures of from 165°–175° C. in cyclohexane using benzene and methyl benzoate chromium tricarbonyl complexes as catalysts).

E. Hydrogenation of Polyunsaturated Oils Using Benzene and Methyl Benzoate Chromium Tricarbonyl Complexes as Catalysts U.S. Pat. No. 3,542,821 to Frankel, issued Nov. 24, 1970, discloses the partial hydrogenation of polyunsaturated vegetable oils such as soybean oil and safflower oil, and mixed methyl esters of such oils, using benzene and methyl benzoate chromium tricarbonyl complexes as catalysts. The hydrogenations were carried out at temperatures of from 145°–175° C. for 2–6 hours (typically 4–6 hours at the lower temperatures). The trans-unsaturate content of the partially hydrogenated oils ranged from 2–9.5% and more typically from 3–9%. See also Frankel, "Conversion of Polyunsaturates and Vegetable Oils to cis-Monounsaturates by Homogeneous Hydrogenation Catalyzed with Chromium Carbonyls," *J. Am. Oil Chem. Soc.*, Vol. 47, (1970), pp. 11–14 (similar disclosure); Frankel et al., "Stereoselective Hydrogenation of Model Compounds and Preparation of Taylor-Made Glycerides with Chromium Tricarbonyl Complexes," *J. Am. Oil Chem. Soc.*, Vol. 47, (1970), pp. 497–500 (hydrogenation of vegetable oils using benzene and methyl benzoate chromium tricarbonyl complexes as catalysts to make simulated olive oil, peanut oil and safflower oil).

DISCLOSURE OF THE INVENTION

The present invention relates to fluoronaphthalene chromium tricarbonyls useful as hydrogenation catalysts for polyunsaturated fatty acid residue-containing compositions. Compositions suitable for hydrogenation by these catalysts comprise glycerides, non-glyceride esters, or mixtures thereof having polyunsaturated fatty acid residues, in particular polyunsaturated vegetable oils and those containing methyl linoleate. After being placed in a reactor having an inert inner surface, the polyunsaturated fatty acid residue-containing composition is contacted with hydrogen in the presence of a catalytic amount of the catalyst $[Cr(A)(CO)_3]$, A being a fluoronaphthalene of formula:

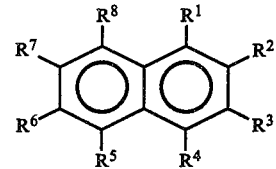

wherein one of $R^1$ and $R^2$ are F, the other of $R^1$ and $R^2$ being F, H, $C_1$–$C_4$ alkyl, or $C_1$–$C_4$ alkoxy; and $R^3$, $R^4$, $R^5$, $R^6$, $R^7$ and $R^8$ are H, $C_1$–$C_4$ alkyl, or $C_1$–$C_4$ alkoxy. As a result, the polyunsaturated fatty acid residues of the composition are hydrogenated, usually to the cis-monounsaturates.

The fluoronaphthalene catalysts of the present invention have a number of advantages, especially with regard to prior art catalysts used in the hydrogenation of polyunsaturated vegetable oils and methyl linoleate. In particular, the fluoronaphthalene catalysts used in the method of the present invention provide much more effective hydrogenation of polyunsaturated fatty acid residues at lower temperatures, especially at temperatures of from about 120° to about 140° C. As a result, there is significantly less isomerization of the polyunsaturated fatty acid residues to the respective trans-unsaturates. Typically, less than about 1% trans-unsaturates are formed in the hydrogenation method of the present invention.

A. Polyunsaturated Fatty Acid Residue-Containing Compositions

The compositions suitable for hydrogenation according to the method of the present invention comprise glycerides, non-glyceride esters, or mixtures thereof which have polyunsaturated fatty acid residues. As used herein, the term "glycerides" refers to monoglycerides, diglycerides, and especially triglycerides, or mixtures thereof. As used herein, the term "non-glyceride esters" refers to fatty acid esters which are not monoglycerides, diglycerides or triglycerides. As used herein, the term "polyunsaturated fatty acid residue" refers to that portion of the glyceride or non-glyceride ester which has the formula:

wherein R is a $C_6$–$C_{22}$ aliphatic hydrocarbyl radical which has at least two double bonds.

The polyunsaturated fatty acid residue can be either conjugated or nonconjugated. As used herein, the term "conjugated polyunsaturated fatty acid residue" refers to those residues where the double bonds alternate with single bonds as represented by the following:

—CH=CH—CH=CH—
or
—CH=CH—CH=CH—CH=CH—

Examples of conjugated polyunsaturated fatty acid residues include 2,4-hexadienoate(sorbate), 4-methyl-2,4-heptadienoate, 9,11-octadecadienoate, 10,12-octadecadienoate, 9,11,13-octadecadienoate(eleostearate), and the like.

As used herein, the term "nonconjugated polyunsaturated fatty acid residue" refers to those residues where the double bonds are separated by a methylene(—$CH_2$—) group as represented by the following:

—CH=CH—CH$_2$—CH=CH—
or
—CH=CH—CH$_2$—CH=CH—CH$_2$—CH=CH—

Particularly preferred nonconjugated polyunsaturated fatty acid residues are linoleic acid residues having the formula:

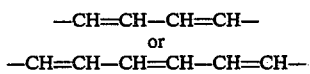

or linolenic acid residues having the formula:

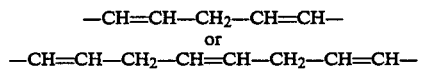

Compositions suitable in the method of the present invention usually consist essentially of glycerides, non-glyceride esters or mixtures thereof which have at least about 20% polyunsaturated fatty acid residues. As used herein, the term "at least about 20% polyunsaturated fatty acid residues" refers to a composition wherein at least about 20% by weight of the fatty acid residues of the glycerides or non-glyceride esters are polyunsaturated fatty acid residues. Glycerides and non-glyceride esters having other fatty acid residues (e.g. oleic, palmitic, stearic) can be included in such compositions, so long as at least about 20% of the total fatty acid residues are polyunsaturated fatty acid residues.

Of the polyunsaturated fatty acid residue-containing compositions consisting essentially of glycerides, the polyunsaturated vegetable oils are most preferred. Representative examples of polyunsaturated oils for which the method of the present invention is suitable include corn oil, cottonseed oil, linseed oil, peanut oil, safflower oil, sesame seed oil, sorghum oil, soybean oil, and sunflower seed oil. The method of the present invention is especially suitable for those polyunsaturated vegetable oils having at least about 50% combined linoleic and linolenic acid residues, in particular, corn oil, soybean oil, safflower oil and sunflower seed oil.

Of the compositions consisting essentially of non-glyceride esters, the preferred ones are those containing linoleate and linolenate esters having the following formulas:

or

wherein R' is a hydrocarbyl group which can be easily removed by hydrolysis. Suitable hydrocarbyl groups include $C_1$–$C_4$ alkyl groups and phenyl groups. A particularly preferred non-glyceride ester is methyl linoleate (R' is methyl). A suitable source of methyl linoleate is the mixture of methyl non-glyceride esters obtained after esterifying the fatty acids present in tall oil with methanol using an acid catalyst such as sulfuric acid. Such a mixture usually contains at least about 30% methyl linoleate. Typically, methyl linoleate (99% purity) can be hydrogenated according to the method of the present invention to at least about 95% methyl isooleates. As used herein, the term "isooleates" refers to a mixture of 9-octadecenoate, 10-octadecenoate, 11-octadecenoate and 12-octadecenoate, typically in a 1:1:1:1 (equimolar) ratio.

B. Fluoronaphthalene Chromium Tricarbonyl Hydrogenation Catalysts

The hydrogenation catalysts useful in the method of the present invention are fluoronaphthalene chromium tricarbonyls. As used herein, the term "fluoronaphthalene chromium tricarbonyls" refers to chromium tricarbonyl complexes of formula [Cr(A)(CO)$_3$], A being a fluoronaphthalene of formula:

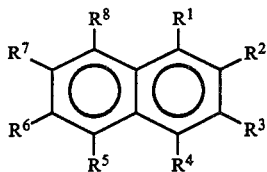

wherein one of $R^1$ and $R^2$ are fluorine (F), the other of $R^1$ and $R^2$ being F, hydrogen (H), $C_1$-$C_4$ alkyl, or $C_1$-$C_4$ alkoxy; and $R^3$, $R^4$, $R^5$, $R^6$, $R^7$ and $R^8$ are H, $C_1$-$C_4$ alkyl, or $C_1$-$C_4$ alkoxy. Preferred fluoronaphthalenes are those wherein only one of $R^1$ or $R^2$ are F, the other of $R^1$ and $R^2$ being H, methyl or methoxy; and $R^3$, $R^4$, $R^5$, $R^6$, $R^7$ and $R^8$ are H, methyl, or methoxy. Alpha-fluoronaphthalene ($R^1$ is F; $R^2$, $R^3$, $R^4$, $R^5$, $R^6$, $R^7$ and $R^8$ are each H), and beta-fluoronaphthalene ($R^2$ is F; $R^1$, $R^3$, $R^4$, $R^5$, $R^6$, $R^7$ and $R^8$ are each H) are especially preferred for catalysts used in the method of the present invention.

A catalytic amount of the fluoronaphthalene chromium tricarbonyl is used in the method of the present invention. What is "a catalytic amount" can vary depending upon the type of fluoronaphthalene chromium tricarbonyl used, the polyunsaturated fatty acid residue-containing composition being hydrogenated, the particular reaction conditions during hydrogenation (e.g., temperature), the degree of hydrogenation desired, and like factors. An amount of from about 0.5 to about 20 mole percent is usually suitable for hydrogenation. However, an amount of from about 5 to about 15 mole percent typically provides optimum hydrogenation of the polyunsaturated fatty acid residues. As used herein, mole percentages given for the fluoronaphthalene chromium tricarbonyl are based on the amount of the polyunsaturated fatty acid residue-containing composition being hydrogenated.

The fluoronaphthalene chromium tricarbonyls used in the method of the present invention can be prepared by refluxing the particular fluoronaphthalene with chromium hexacarbonyl in a high boiling solvent such as heptane or di-n-butyl ether. See Cais et al., "The Catalytic Activity of Tricarbonyl Chromium Complexes of Phenanthrene, Naphthalene and Anthracene in the Hydrogenation of Dienes," *Coord. Chem. Rev.*, Vol. 16, (1975), p. 29. See also Mahaffy et al., "(n6-Arene)tricarbonylchromium Complexes," *Inorganic Synthesis*, Vol. 19, (1979), pp. 154–58, which discloses a synthesis procedure for simple arene(benzene)-chromium tricarbonyls which can be modified to prepare fluoronaphthalene chromium tricarbonyls. A general synthesis procedure for these fluoronapthalene chromium tricarbonyl catalysts is as follows:

In a 500 ml round bottom flask, 10 g of chromium hexacarbonyl and 1.1 equivalents of the particular fluoronaphthalene are suspended in 300 ml of di-n-butyl ether and 30 ml of tetrahydrofuran (THF) as the solvent. The flask is equipped with an air condenser and a water-cooled Friedricks condenser. This system is vented through an oil bubbler and purged with dry, purified nitrogen gas. The contents of the flask are heated to reflux for 12 to 24 hours and become deep orange to deep red as the reaction proceeds. At the end of the reaction, the solvent, unreacted fluoronaphthalene, and unreacted chromium hexacarbonyl are removed in vacuuo. The fluoronaphthalene chromium tricarbonyl formed is then purified, if necessary, by recrystallization from hexane. Yields of the catalyst can range from 65 to 93% depending on the reaction time and the particular fluoronaphthalene.

C. Reaction Conditions During Hydrogenation

Normally, the polyunsaturated fatty acid residue-containing composition is liquid at ambient temperatures (20°–25° C.). For example, polyunsaturated vegetable oils such as soybean oil and methyl linoleate are all liquids. Accordingly, a reaction mixture suitable for hydrogenation can be formed by simply mixing together the liquid polyunsaturated fatty acid residue-containing composition and the fluoronaphthalene chromium tricarbonyl. If desired, nonpolar, nonreactive solvents can be used. Examples of suitable solvents for the method of the present invention include aliphatic hydrocarbon solvents such as hexane, heptane and the like. Examples of solvents which should not be used include arene (aromatic) solvents such as benzene, ketone solvents such as acetone, tetrahydrofuran, ethyl acetate and the like which can exchange with the fluoronaphthalene and thus become bound to the chromium tricarbonyl catalyst. In the case of polyunsaturated vegetable oils, hydrogenation is typically carried out in the absence of solvent, i.e. as a neat reaction.

To effect hydrogenation of the polyunsaturated fatty acid residues, the reaction mixture is contacted with hydrogen. The hydrogen pressure is generally not critical to the method of the present invention as long as it is greater than the partial pressure of any solvent being used. A hydrogen pressure of at least about 50 psi is usually suitable in the method of the present invention. Typically, the hydrogen pressure is from about 100 to about 500 psi.

While being contacted with hydrogen, the reaction mixture is heated to the appropriate temperature. The particular temperature required for hydrogenation is dependent upon the particular polyunsaturated fatty acid residues present in the reaction mixture. For conjugated polyunsaturated fatty acid residues, lower temperatures are suitable for hydrogenation. Usually, a temperature of at least about 40° C. is sufficient for the hydrogenation of a reaction mixture containing such residues. An optimum temperature range for the hydrogenation of such residues is typically from about 60° to about 100° C.

For nonconjugated polyunsaturated fatty acid residues, much higher temperatures are required. Usually, a reaction mixture containing such residues is heated to a temperature of from about 80° to about 160° C. Temperatures much below about 80° C. do not provide effective hydrogenation of nonconjugated polyunsaturated fatty acid residues. Temperatures much above about 160° C. can cause significant amounts of trans-unsaturates to be formed due to isomerization of the polyunsaturated fatty acid residues. Temperatures of from about 120° to about 140° C. typically provide optimum hydrogenation of the nonconjugated polyunsaturated fatty acid residues without significant formation of trans-unsaturates, i.e. typically less than about 1% trans-unsaturates are formed.

Hydrogenation is carried out for a period of time sufficient to provide the desired degree of hydrogenation of the polyunsaturated fatty acid residues. The degree of hydrogenation desired often depends on the polyunsaturated fatty acid residue-containing composition being hydrogenated and the particular use of the hydrogenated composition. For compositions containing methyl linoleate, such as the mixed methyl esters of tall oil which are hydrolyzed to obtain isooleic acids, a higher degree of hydrogenation is desired. For example, methyl linoleate is typically hydrogenated for from about 0.5 to about 2 hours to provide at least about 95% methyl isooleates. For polyunsaturated vegetable oils such as soybean, safflower and sunflower seed oils which require oxidative flavor stability, partial hydrogenation is usually sufficient. For example, these oils, which typically contain at least about 50% combined linoleic and linolenic acid residues, can be partially hydrogenated for from about 0.5 to about 2 hours to provide from about 20 to about 30% combined linoleic and linolenic acid residues.

Hydrogenation according to the method of the present invention is carried out in a reactor which has an inert inner surface. As used herein, the term "reactor which has an inert inner surface" refers to a reactor which has an inner surface that does not interfere with or deactivate the fluoronaphthalene chromium tricarbonyls used as hydrogenation catalysts. Suitable reactors include those made totally out of an inert material such as glass reactors or those which have an inert inside lining, such as glass-lined or polytetrafluoroethylene (Teflon)-lined reactors. In addition to higher temperatures, it is also believed that prior art benzene and benzoate chromium tricarbonyl catalysts require unlined steel reactors in order to effectively catalyze the hydrogenation of polyunsaturated vegetable oils or methyl linoleate. For example, it has been found that there is no measurable yield of methyl isooleates after 2 hours when methyl linoleate is hydrogenated in a glass-lined reactor using either benzene or methyl benzoate chromium tricarbonyl as the catalyst. By contrast, the fluoronaphthalene chromium tricarbonyls used in the method of the present invention are effective hydrogenation catalysts in a glass or glass-lined reactor, i.e. when free of contact with iron. Indeed, it has been found that unlined, stainless steel reactors can cause deactivation of the naphthalene chromium tricarbonyls during the hydrogenation of methyl linoleate.

CONVERSION OF METHYL ISOOLEATES TO ISOOLEIC ACIDS

In the case of polyunsaturated vegetable oils used in edible oil applications such as cooking oil and salad oil preparation, the glycerides are used as is after hydrogenation. However, in the case of hydrogenated compositions containing methyl isooleates such as the hydrogenated mixed methyl esters of tall oil (typically greater than 95% methyl isooleates), the non-glyceride esters are typically hydrolyzed to yield isooleic acids. Hydrolysis of the esters can be achieved using standard saponification reaction conditions. For example, the hydrogenated composition can be mixed with an ethanolic solution of base such as sodium or potassium hydroxide and water. This solution is then refluxed for a period of time sufficient to hydrolyze the esters to yield the respective fatty acids, in particular the isooleic acids. This hydrolyzed solution is neutralized with acid and then extracted with an organic solvent to partition the fatty acids, including the isooleic acids, into the organic layer. The organic solvent can be evaporated to yield a crude mixture containing a high percentage of isooleic acids. If desired, this crude mixture can be fractionally distilled to yield a purer mixture of isooleic acids. Commercial hydrolyzers can also be used to obtain isooleic acids from the hydrogenated composition.

SPECIFIC ILLUSTRATIONS OF THE HYDROGENATION OF METHYL LINOLEATE USING FLUORONAPHTHALENE CHROMIUM TRICARBONYL AS CATALYSTS

The following examples of the hydrogenation of methyl linoleate (greater than 99% pure) to methyl isooleates using fluoronaphthalene chromium tricarbonyls as the catalyst are used to illustrate the method of the present invention:

All hydrogenations were carried out in a reactor which was either: (1) a 50 ml Griffen-Worden (G-W) glass pressure vessel shaken in a thermostatically controlled oil bath; or (2) a 300 ml Autoclave Engineers (AE) rocking autoclave fitted with a glass liner which was electrically heated and controlled. A reaction mixture containing 0.5 g (G-W) or 2 g (AE) of methyl linoleate in hexane (0.03 to 0.04M) and a measured amount of catalyst was placed in the reactor. The reaction mixture was then placed under a hydrogen atmosphere at the appropriate hydrogen pressure. The reaction mixture was stirred under this hydrogen atmosphere at the desired temperature for 0.5 hours. At the end of this 0.5 hour period, a sample was taken from the reaction mixture for analysis by gas chromatography to determine the yield of methyl isooleates and by quantitative IR to determine the level of trans-unsaturates.

A. Catalyst

The yield of methyl isooleates from the hydrogenation (200 psi hydrogen pressure, G-W reactor) of methyl linoleate at 135° C. for 0.5 hours using different fluoronaphthalene chromium tricarbonyl catalysts (10 mole percent) is shown in the following table:

| Catalyst | Isooleates (%) | Trans-unsaturates (%) |
|---|---|---|
| Alpha-fluoronaphthalene | >95 | <1 |
| Beta-fluoronaphthalene | >95 | <1 |

B. Reaction Temperatures

The yield of methyl isooleates from the hydrogenation (200 psi hydrogen pressure, G-W reactor) of methyl linoleate using alpha-fluoronaphthalene chromium tricarbonyl (10 mole percent) as the catalyst for 1 hour at different reaction temperatures is shown in the following table:

| Temperature (°C.) | Isooleates (%) | Trans-unsaturates (%) |
|---|---|---|
| 100 | 57 | <1 |
| 120 | 83 | <1 |
| 135 | 98 | <1 |
| 160 | 97 | 3 |

C. Hydrogen Pressure

The yield of methyl isolates from the hydogenation of methyl linoleate using alpha-fluoronaphthalene chromium tricarbonyl (10 mole percent) as the catalyst at 135° C. for 1 hour at different hydrogen pressures is shown in the following table:

| Hydrogen Pressure (psi) | Isooleate (%) | Trans-unsaturates (%) |
|---|---|---|
| 50* | 98 | <1 |
| 100** | 98 | <1 |

-continued

| Hydrogen Pressure (psi) | Isooleate (%) | Trans-unsaturates (%) |
|---|---|---|
| 200** | 98 | <1 |
| 500** | 98 | <1 |
| 2000** | 98 | <1 |

*G-W reactor
**AE reactor

D. Catalyst Levels

The yield of methyl isooleates from the hydrogenation (200 psi hydrogen pressure, G-W reactor) of methyl linoleate at 100° C. for 1 hour using different levels of alpha-fluoronaphthalene chromium tricarbonyl as the catalyst is shown in the following table:

| Catalyst Level (mole %) | Isooleates (%) | Trans-unsaturates (%) |
|---|---|---|
| 1.0 | 8.5 | <1 |
| 2.5 | 26 | <1 |
| 5.0 | 40 | <1 |
| 10.0 | 55 | <1 |

COMPARISON OF ALPHA-FLUORONAPHTHALENE CHROMIUM TRICARBONYL TO PRIOR ART BENZENE, METHYL BENZOATE AND FLUOROBENZENE CHROMIUM TRICARBONYLS AS HYDROGENATION CATALYSTS

Alpha-fluoronaphthalene chromium tricarbonyl was compared to prior art benzene, methyl benzoate and fluorobenzene chromium tricarbonyls as hydrogenation catalysts. The yield of methyl isooleates from the hydrogenation (100 psi hydrogen pressure, G-W reactor) of methyl linoleate using each catalyst (10 mole percent) at different reaction temperatures for 2 hours is shown in the following table:

| Catalyst | Reaction Temp. (°C.) | Isooleates (%) | Trans-unsaturates (%) |
|---|---|---|---|
| benzene | 120 | 0 | — |
|  | 135 | 0 | — |
|  | 160 | 0 | — |
| benzoate | 120 | 0 | — |
|  | 135 | 0 | — |
|  | 160 | 0 | — |
| fluoro-benzene | 120 | 0 | — |
|  | 135 | 0 | — |
|  | 160 | 14 | 9 |
| alpha-fluoro-naphthalene | 120 | 98 | <1 |
|  | 135 | 99 | <1 |
|  | 160 | 96 | 4 |

SPECIFIC ILLUSTRATION OF THE HYDROGENATION OF SOYBEAN OIL USING ALPHA-FLUORONAPHTHALENE CHROMIUM TRICARBONYL AS CATALYST

The following example of the hydrogenation of soybean oil using alpha-fluoronaphthalene chromium tricarbonyl as the catalyst is used to illustrate the hydrogenation of polyunsaturated vegetable oils according to the present invention:

A 0.5 g. portion of soybean oil (iodine value of 140) and 10 mole % of the catalyst was placed in a G-W reactor. This mixture was then placed under a 200 psi hydrogen atmosphere. The mixture was stirred under this hydrogen atmosphere for 2 hours at 135° C. At the end of this period, the mixture was filtered through $Al_2O_3$ (to remove the catalyst), washed with hexane and then evaporated to dryness. The hydrogenated oil was taken up in methanol and transesterified with a $BF_3.MeOH$ complex. The methanol solution was diluted with hexane, washed with $H_2O$, $NaHCO_3$ solution and $H_2O$, and then dried with $Na_2SO_4$. The results of the GC analysis of this hexane solution containing the methyl esters of the hydrogenated oil and the methyl esters of the starting soybean oil are presented in the following Table:

| Fatty Acid of Ester | Soybean Oil (mole %) | Hydrogenated Oil (mole %) |
|---|---|---|
| C18:0 | 4.0 | 4.7 |
| trans-C18:1 | 0 | 5.5 |
| cis-C18:1 | 21.3 | 72.9 |
| C18:2 | 55.3 | 3.0 |
| C18:3 | 7.4 | 0.2 |
| conjugated-C18:2 | 0.1 | 0 |
| Iodine value | 140 | 75 |

What is claimed is:

1. A method for hydrogenating the polyunsaturated fatty acid residues of a polyunsaturated fatty acid residue-containing composition, which comprises the steps of:
   (1) placing in a reactor having an inert inner surface a polyunsaturated fatty acid residue-containing composition comprising glycerides, non-glyceride esters, or mixture thereof, having nonconjugated polyunsaturated fatty acid residues; and
   (2) contacting the polyunsaturated fatty acid residue-containing composition with hydrogen at a temperature of from about 100° to about 160° C. in the presence of a catalytic amount of, $[Cr(A)(CO)_3]$, wherein A is selected from the group consisting of alpha-fluoronaphthalene and beta-fluoronaphthalene, to hydrogenate the polyunsaturated fatty acid residues.

2. A method according to claim 1 wherein A is alpha-fluoronaphthalene.

3. A method according to claim 1 wherein A is beta-fluoronaphthalene.

4. A method according to claim 1 wherein said contacting step is carried out at an hydrogen pressure of at least about 50 psi.

5. A method according to claim 4 wherein said contacting step is carried out at an hydrogen pressure of from about 100 to about 500 psi.

6. A method according to claim 1 wherein the amount of $[CR(A)(CO)_3]$ is from about 0.5 to about 20 mole percent.

7. A method according to claim 6 wherein the amount of $[Cr(A)(CO)_3]$ is from about 5 to about 15 mole percent.

8. A method according to claim 1 wherein the polyunsaturated fatty acid residues are selected from the group consisting of lineolic acid residues, linoleic acid residues and mixtures thereof.

9. A method according to claim 8 wherein the polyunsaturated fatty acid residue-containing composition consists essentially of glycerides, non-glyceride esters, or mixtures thereof, having at least about 20% polyunsaturated fatty acid residues.

10. A method according to claim 9 wherein the polyunsaturated fatty acid residue-containing composition consists essentially of non-glyceride esters.

11. A method according to claim 10 wherein the polyunsaturated fatty acid residue-containing composition has at least about 30% methyl linoleate.

12. A method according to claim 9 wherein the polyunsaturated fatty acid residue-containing composition is a polyunsaturated vegetable oil.

13. A method according to claim 12 wherein the polyunsaturated vegetable oil has at least about 50% combined linoleic and linolenic acid residues.

14. A method according to claim 13 wherein the polyunsaturated vegetable oil is selected from the group consisting of corn oil, soybean oil, safflower oil and sunflower seed oil.

15. A method for hydrogenating the polyunsaturated fatty acid residues of a polyunsaturated fatty acid residue-containing composition, which comprises the steps of:

(1) placing in a reactor having an inert inner surface a polyunsaturated fatty acid residue-containing composition consisting essentially of glycerides, non-glyceride esters, or mixtures thereof, having at least about 20% polyunsaturated fatty acid residues selected from the group consisting of linoleic acid residues, linolenic acid residues and mixtures thereof; and (2) contacting the polyunsaturated fatty acid residue-containing composition with hydrogen at an hydrogen pressure of from about 100 to about 500 psi and at a temperature of from about 120° to about 140° C. in the presence of from about 5 to about 15 mole percent of [Cr(A)(CO)$_3$], wherein A is selected from the group consisting of alpha-fluoronaphthalene and beta-fluoronaphthalene, to hydrogenate the polyunsaturated fatty acid residues.

16. A method according to claim 15 wherein the polyunsaturated fatty acid residue-containing composition consists essentially of non-glyceride esters.

17. A method according to claim 16 where in the polyunsaturated fatty acid residue-containing composition has at least about 30% methyl linoleate.

* * * * *

UNITED STATES PATENT AND TRADEMARK OFFICE
CERTIFICATE OF CORRECTION

PATENT NO. : 4,590,007
DATED : May 20, 1986
INVENTOR(S) : James R. Tucker, Dennis P. Riley It is certified that error appears in the above-identified patent and that said Letters Patent are hereby corrected as shown below:

Column 6, line 61, "Cataysts" should be --Catalysts--.

Column 12, line 59, "lineolic" should be --linoleic--.

Column 12, line 59, "linoleic" should be --linolenic--.

Signed and Sealed this

Twentieth Day of September, 1988

Attest:

DONALD J. QUIGG

Attesting Officer

Commissioner of Patents and Trademarks